US007132453B2

(12) United States Patent
Peebles, Jr. et al.

(10) Patent No.: US 7,132,453 B2
(45) Date of Patent: Nov. 7, 2006

(54) METHOD OF USING PROSTACYCLIN TO TREAT RESPIRATORY SYNCYTIAL VIRUS INFECTIONS

(75) Inventors: Ray Stokes Peebles, Jr., Nashville, TN (US); Koichi Hashimoto, Kohriyama Fukushima (JP); Barney S. Graham, Rockville, MD (US)

(73) Assignee: Vanderbilt University, Nashville, TN (US)

( * ) Notice: Subject to any disclaimer, the term of this patent is extended or adjusted under 35 U.S.C. 154(b) by 146 days.

(21) Appl. No.: 10/389,295

(22) Filed: Mar. 14, 2003

(65) Prior Publication Data

US 2003/0216474 A1    Nov. 20, 2003

Related U.S. Application Data

(60) Provisional application No. 60/364,395, filed on Mar. 15, 2002.

(51) Int. Cl.
*A01N 37/08* (2006.01)
*A01N 53/00* (2006.01)
*A61K 31/19* (2006.01)
*A61K 31/557* (2006.01)

(52) U.S. Cl. .................. 514/573; 554/117; 549/422

(58) Field of Classification Search ................ 514/464, 514/719, 569, 468, 573
See application file for complete search history.

(56) References Cited

U.S. PATENT DOCUMENTS

2001/0044467 A1 * 11/2001 Neal ........................... 514/573

FOREIGN PATENT DOCUMENTS

EP          0671410 A1      7/1990
GB          2 166 050 A   *  4/1986

OTHER PUBLICATIONS

Miyamori et al, 95CA:109278, 1984.*
Zavagno, et al., *Role of Prostaglandins and Non-steroid Anti-inflammatory Drugs in the Pathogenicity of Vaccinia Virus*, Journal of General Virology (1987) 68:593-600. SGM, Great Britain (The year of publication is sufficiently earlier than the effective U.S. filing date and any foreign priority date so that the particular month of publication is not in issue).
Patterson, J.H., et al., *Acute Hemodynamic Effects of the Prostacyclin Analog 15AU81 in Severe Congestive Heart Failure*, American Journal of Cardiology (Jan. 1995) 75:26A-33A, Excerpta Medica, USA. (ABSTRACT only).
Belch, J.J., et al., *Oral Iloprost As a Treatment for Raynaud's Syndrome: A Double Blind Multicentre Placebo Controlled Study*, Annals of Rheumatic Diseases (Mar. 1995) 54:197-2000, BMJ Publishing Group, UK.. (ABSTRACT only).
Saji, et al., *Short-Term Hemodynamic Effect of a New Oral PGI2 Analogue, Beraprost, in Primary and Secondary Pulmonary Hypertension*, American Journal of Cardiology (Jul. 1996) 78:244-247, Excerpta Medica, Inc., USA.
Higenbottam, et al., *Treatment of Pulmonary Hypertension with the Continuous Infusion of a Prostacyclin Analogue, Iloprost*, Heart (1998) 79:175-179, BMJ Publishing Group, UK (The year of publication is sufficiently earlier than the effective U.S. filing date and any foreign priority date so that the particular month of publication is not is issue).
Higenbottam, et al., *Long Term Intravenous Prostaglandin (epoprostenol or Iloprost) for treatment of Severe Pulmonary Hypertension*, Heart (1998) 80:151-155, BMJ Publishing Group, UK (The year of publication is sufficiently earlier than the effective U.S. filing date and any foreign priority date so that the particular month of publication is not in issue).
Fink, et al., *Use of Prostacyclin and its Analogues in the Treatment of Cardiovascular Disease*, Heart Disease (1999) 1:29-40, Lippincott Williams & Wilkins, Inc., USA (The year of publication is sufficiently earlier than the effective U.S. filing date and any foreign priority date so that the particular month of publication is not in issue).
Gaine, et al., *Acute Hemodynamic Effects of Subcutaneous UT-15 in Primary Pulmonary Hypertension*, American Journal of Respiratory and Critical Care Medicine (Mar. 1999) 159:A161, American Thoracic Society, USA.
Nagaya, *Effect of Orally Active Prostacyclin Analogue on Survival of Outpatients With Primary Pulmonary Hypertension*, Journal of the American College of Cardiology (Oct. 1999) 34:1188-1192, Elsevier Science, Inc. USA.
Olschewski, et al., *Inhales Iloprost to Treat Severe Pulmonary Hypertension*, Annals of Internal Medicine (Mar. 2000) 132:435-443, American College of Physicians—American Society of Medicine, USA.
Max et al, "Inhaled prostacyclin in the treatment of pulmonary hyerptension", European Journal of Pediatrics 1999 vol. 158 (suppl. J), s23-s26, CAPLUS Abstract AN, 1999:809374.

* cited by examiner

*Primary Examiner*—Sreenivasan Padmanabhan
*Assistant Examiner*—Leonard Williams
(74) *Attorney, Agent, or Firm*—Wyatt, Tarrant & Combs, LLP

(57) ABSTRACT

The present invention discloses methods and a kit for treating a respiratory syncytial virus infection. The method comprises providing an infection modulator, and administering a therapeutically effective amount of the infection modulator, wherein the respiratory syncytial virus infection is suppressed or precluded. The kit for suppressing a respiratory syncytial virus infection comprises an infection modulator, an applicator, and a set of instructions.

15 Claims, 9 Drawing Sheets

METHOD OF USING PROSTACYCLIN TO TREAT RESPIRATORY SYNCYTIAL VIRUS INFECTIONS

This patent application claims benefit of co-pending U.S. Provisional Patent Application No. 60/364,395 filed on Mar. 15, 2002 entitled "Method of Using Prostacyclin to Treat Respiratory Syncytial Virus Infections," which is incorporated herein by reference.

Be it known that we Ray Stokes Peebles, Jr., M.D., a United States citizen, of 3816 Hobbs Road, Nashville, Tenn. 37215, Koichi Hashimoto, M.D., a Japanese citizen, of 63 Azuma Fukuhara Fukuyama Kohriyama Fukushima, Japan 9638061, and Barney S. Graham, M.D., Ph.D., a United States citizen, of 301 Pure Spring Crescent, Rockville, Md. 20850-5694, have invented a new and useful "Method of Using Prostacyclin to Treat Respiratory Syncytial Virus Infections."

GOVERNMENT SUPPORT CLAUSE

This invention was made with federal grant money under NIH grant R01-AI-45512 and K08-HL-03730. The United States Government has certain rights in this invention.

FIELD OF THE INVENTION

This invention relates generally to compositions and methods for treating or reducing the onset of symptoms of respiratory diseases caused by viral infections. More specifically, this invention relates to compositions and methods for treating respiratory syncytial virus (RSV).

BACKGROUND OF THE INVENTION

Respiratory syncytial virus is the principal cause of hospitalization for respiratory tract illness in young children, the most common cause of respiratory failure in infants and is the leading infectious cause of wheezing and asthma exacerbations in children under two years of age, extensively reviewed in Hall CB, 2001, N. Engl. J. Med., 344:1917–1928. In addition, RSV is the second most common infectious agent that causes wheezing in adults over 65 years old and can also cause severe pneumonia in this age group. For each year in the decade 1980–90, RSV infection led to the hospitalization of approximately 100,000 children for a cost of over $300 million. Currently, there is no effective vaccine for RSV and pharmacological treatment is far from optimal. Development of new therapeutic agents and vaccine approaches hold the promise of reducing morbidity and mortality from this important pathogen.

RSV is an enveloped RNA virus of the Paramyxoviridae family and has a nonsegmented, single-stranded, negative sense genome. The genome of RSV encodes 10 proteins, of which two are nonstructural. Critical to RSV-induced immunity and pathogenesis are the large envelope glycoproteins, which are the fusion protein (F) and the attachment protein (G). Variations in the G protein distinguish the two major groups of RSV strains, A and B, although there are a few differences in the F protein between the two strains.

RSV infections occur most commonly between November and May each year in the US, with a peak of frequency in January to February. Illness with the A strain is more common, but both strains cause illness during the same months of the year. Within the strains, there can be genotypic differences that more commonly cause illness within a specific community, and these strains can vary yearly, providing a possible mechanism by which previous infection may not lead to immunity. Reinfection occurs quite commonly with RSV, and lower respiratory symptoms are three-to-four more frequent with RSV reinfection compared to another respiratory virus, such as parainfluenza virus. Reinfections are not limited to children, as RSV accounts for about 21% of acute respiratory infections in the elderly attending senior day care.

Following two to eight days of incubation, RSV replicates in the epithelium of the nasopharynx and then may spread to the lower respiratory tract one-to-three days later. The pathologic features of bronchiolitis caused by RSV include epithelial necrosis and sloughing in the small airways, edema in the walls of the small airways, and increased mucus production. These three consequences of RSV infection can lead to airflow obstruction within the small airways, resulting in hyperinflation, atelectasis, and wheezing. In adults with severe pneumonia caused by RSV, radiographic findings include interstitial and alveolar infiltrates with consolidation. On histologic examination, the bronchiolitis may resolve within several days of the onset of illness; however, repopulation of ciliated epithelial cells generally does not occur for at least two weeks, and complete resolution of the cellular changes may take four to eight weeks. The histologic abnormalities correlate with the prolonged clinical course of cough, wheezing, and decreased pulmonary function.

The virus is transmitted through direct inoculation of secretions containing RSV via the hands or large particle aerosols into the eyes and nose, and very infrequently the mouth. From studies investigating the spread of RSV within the hospital, it seems that transmission of the virus necessitates close or direct contact with large droplets or fomites. RSV can also live on skin, cloth, and other objects for extended periods of time, extending the possibility of transmission of infection.

Approximately 70% of people are infected with RSV in the first year of life and almost everyone has been infected by age 3. Although the majority of people have self-limited disease, RSV is a significant respiratory tract pathogen and is a major cause of hospitalization in children. Whereas parainfluenza infection results in a hospitalization rate of 2.8 per 1,000 infections, the rate of hospitalization for RSV is roughly four-fold higher at 10 per 1,000. In hospitalized children, RSV is cultured in 50–90% of patients with bronchiolitis, 5–40% with pneumonia, and 10–30% with tracheobronchitis. In patients with cystic fibrosis, RSV accounts for 43% of hospital admissions for viral infections, more than any other virus. In adults, up to 4.4% of patients admitted to the hospital for community-acquired pneumonia have RSV identified from respiratory secretions. Chest radiographs in patients with RSV induced pneumonia may be misidentified as being of bacterial etiology since lobar consolidation can occur in up to one-third of patients.

RSV is also an important cause of wheezing and asthma exacerbations in both young children and older adults. RSV is the most frequent respiratory pathogen detected in children less than 2 years of age that present to the emergency department for wheezing. In infants who are hospitalized with RSV bronchiolitis, there is a significant association with the development of asthma and allergic sensitization up to age 7. In addition, RSV lower respiratory tract illness before 3 years of age is an independent risk factor for the subsequent development of wheezing up to 11 years of age, but not age 13, and this association is not caused by an increased risk of allergic sensitization. Admission to the hospital for RSV-induced wheezing is also not limited to children, as RSV is identified in between 5–50% of patients admitted for exacerbations of chronic obstructive lung disease, with a mortality in these patients that is almost 20%.

RSV has been identified as an important cause of death among immunocompromised patients. In patients receiving immunosuppression for transplants, RSV infection has a 30–100% mortality rate. Often, these infections are transmitted to the patient from visitors or hospital staff who are experiencing an upper respiratory tract infection and be initially thought to be a relatively inconsequential illness because of the mild symptoms at the beginning of the infection. However, RSV can lead to severe pulmonary symptoms in the transplant patient with chest radiographs showing a range of infiltrates including focal interstitial, diffuse alveolar, or dense consolidation. Diagnosis is aided by bronchoscopy with bronchoalveolar lavage, with transbronchial biopsies being performed to rule out other pathogens common in transplant patients such as cytomegalovirus.

As previously mentioned, prior infection does not lead to complete or long-lasting immunity, although prior infection does seem to protect against the development of more severe disease. Vaccines, which have provided protection against other viral illnesses such as small pox, polio, and hepatitis, have a disappointing history in protecting against RSV. In the 1960s, a formalin-inactivated vaccine trial was initiated, which unfortunately led to more severe illness with subsequent RSV infection compared to non-vaccinated subjects. Eighty percent of patients inoculated with the formalin-inactivated vaccine required hospitalization, in comparison to only 5% of controls. Two patients who were vaccinated with the formalin-inactivated preparation died and at autopsy, eosinophilic infiltrates were found in the lung. In other vaccinated patients, peripheral eosinophilia and augmented RSV-induced lymphocytic proliferative responses occurred. Patients receiving the formalin-inactivated vaccine did not have RSV-specific mucosal antibodies, and serum antibodies lacked neutralizing and fusion-inhibiting activity, which inferred that the formalin inactivation selectively modified epitopes within the G and F surface glycoproteins.

The current concept regarding protective immunity is that secretory and serum antibodies protect against upper and lower respiratory infections, while cellular responses are thought to control and terminate infection. RSV-specific serum antibodies do not predict the risk of infection or illness; however, IgG 1 antibodies against F and G have a protective effect against lower, but not upper respiratory illness in rats. Infants that have high levels of maternal antibody, or who are given exogenous antibody, have improved clinical courses compared to those who do not. Cellular-mediated immunity is presumed to be the most beneficial for recovery from illness and viral clearance. Patients who have decreased cellular immune responses have more severe and prolonged disease.

Treatment for RSV illness is currently expensive and sub-optimal. Administration of immune globulin that contains high titers of RSV neutralizing antibody prophylactically to persons at high risk for the complications of RSV disease (premature infants and those with underlying cardiopulmonary conditions) diminishes severity of illness. This requires monthly administration of RSV hyperimmune globulin or monoclonal antibody against F protein and results in decreasing the risk of subsequent hospitalization. Currently, the American Academy of Pediatrics advocates prophylaxis during the RSV season for high-risk infants without cyanotic heart disease, since patients with this condition seem to have an increased risk of adverse outcomes.

At present, aerosolized ribavirin is the only therapy approved by the FDA for the treatment of RSV infection. Ribavirin is a synthetic guanosine analogue and broad-spectrum agent that is indicated for hospitalized infants. Although ribavirin treatment is associated with improved oxygenation and clinical scores, along with a decrease in the inflammatory mediators that associated with more severe disease, ribavirin is very expensive and the beneficial effect on clinical outcome has not been proven.

Nonsteroidal anti-inflammatory drugs (NSAIDs) are commonly used to treat the symptoms of viral upper respiratory tract infections; however, prospective, randomized, double-bind, placebo-controlled trials have not been performed to determine the efficacy of these agents in viral infections in general, nor for specific viruses in particular. The rationale for using this class of medication is that they inhibit the cyclooxygenase enzymes and decrease the production of the prostanoids, a family of arachidonic acid metabolites that mediate inflammation. There are very few animal studies which investigate the effect of NSAIDs on the outcome of viral infections, and, to our knowledge, no published reports that examine the role of this medication class on RSV. Dr. Zavagno and colleagues studied the role of NSAIDs in a murine model (BALB/c) of vaccinia virus infection. Zavagno, et al., 1987, J. Gen. Virol., 68:593–600. These investigators found that mice treated with either aspirin or indomethacin had a marked increase in mortality for vaccinia virus infection over non-treated mice. The mice treated with the NSAIDs had delayed viral clearance with inhibition of the antibody response, whereas control mice that had the higher survival rate had lower virus yield and normal antibody responses.

The effect prostacyclin has on vaccinia virus infections has been reported. Zavagno, et al., 1987, J. Gen. Virol., 68:593–600. However, for the following reasons the results obtained by use of the present invention, disclosed herein, are unexpected as compared to the information provided regarding the vaccinia virus. First, the viruses are from different families. The vaccinia virus is nonenveloped and is a large DNA virus from the Poxvirus family, while RSV is an enveloped RNA virus from the Paramyxovirus family. Viruses are classified based upon the composition of the genomes and the pathway of mRNA formation. Under this classification system, DNA viruses are found within classes I and II, while RNA viruses are present within classes III–VI. Further, the presence of a virus envelop, which consists mainly of a phospholipids bilayer and other glycoproteins, results in a significant difference in the properties of enveloped viruses as compared to nonenveloped viruses. Since RSV is so unique, the invention disclosed herein provides unexpected results. The invention disclosed herein appears to be based upon unknown properties of prostacyclin and prostacyclin analogs. Furthermore, the administration of prostacyclin in the Zavagno study was twice a day. Prostacyclin has a biologic half-life in the 1–2 minute range and therefore the dosing scheme disclosed herein has greater biologic relevance.

Across the United States, about 5,000 children die each year of RSV bronchiolitis. In addition to children, patients who receive solid organ transplants such as lungs or a heart are at an extremely high risk for RSV. Among lung transplant recipients, RSV infection carries about a 50%–75% mortality rate. The current treatment options for RSV are sub-optimal for a number of reasons. Prophylatic administration of the immune globulin that contains high titers of RSV neutralizing antibody to persons at high risk for the complications of RSV disease, such as premature infants and children with underlying cardiopulmonary conditions does diminish illness, but this therapy must be given monthly, is very expensive, and carries the risk of infection of blood products. Therefore novel treatment options need to be developed.

SUMMARY OF THE INVENTION

The present invention discloses a method of treating respiratory syncytial virus infections. The method includes providing an infection modulator and administering a therapeutically effective amount of the infection modulator, wherein the respiratory syncytial virus infection is suppressed. In certain embodiments, the method additionally includes determining that the respiratory syncytial virus infection is suppressed. The murine model is used to evaluate RSV infections since RSV infections in the mouse are very similar immunologically and pathologically to what takes place in humans.

The present invention also discloses a kit for suppressing a respiratory syncytial virus infection. The kit includes an infection modulator, an applicator, and a set of instructions.

Accordingly, one object of the present invention is to provide a method of treating a respiratory syncytial virus infection in order to prevent the suffering or death of a patient.

Another object of the present invention is to provide a method of treating a respiratory syncytial virus infection that is inexpensive.

Still another object of the present invention is to provide a method of treating a respiratory syncytial virus infection that is easy to administer.

Another object of the present invention is to provide a method of treating a respiratory syncytial virus infection that is effective as a preventative against future respiratory syncytial virus infections.

Still another object of the present invention is to provide a kit for treating a respiratory syncytial virus infection that is inexpensive.

Another object of the present invention is to provide a kit for treating a respiratory syncytial virus infection that is easily administered in a non-hospital setting.

DESCRIPTION OF THE PREFERRED EMBODIMENTS

Figure 1:
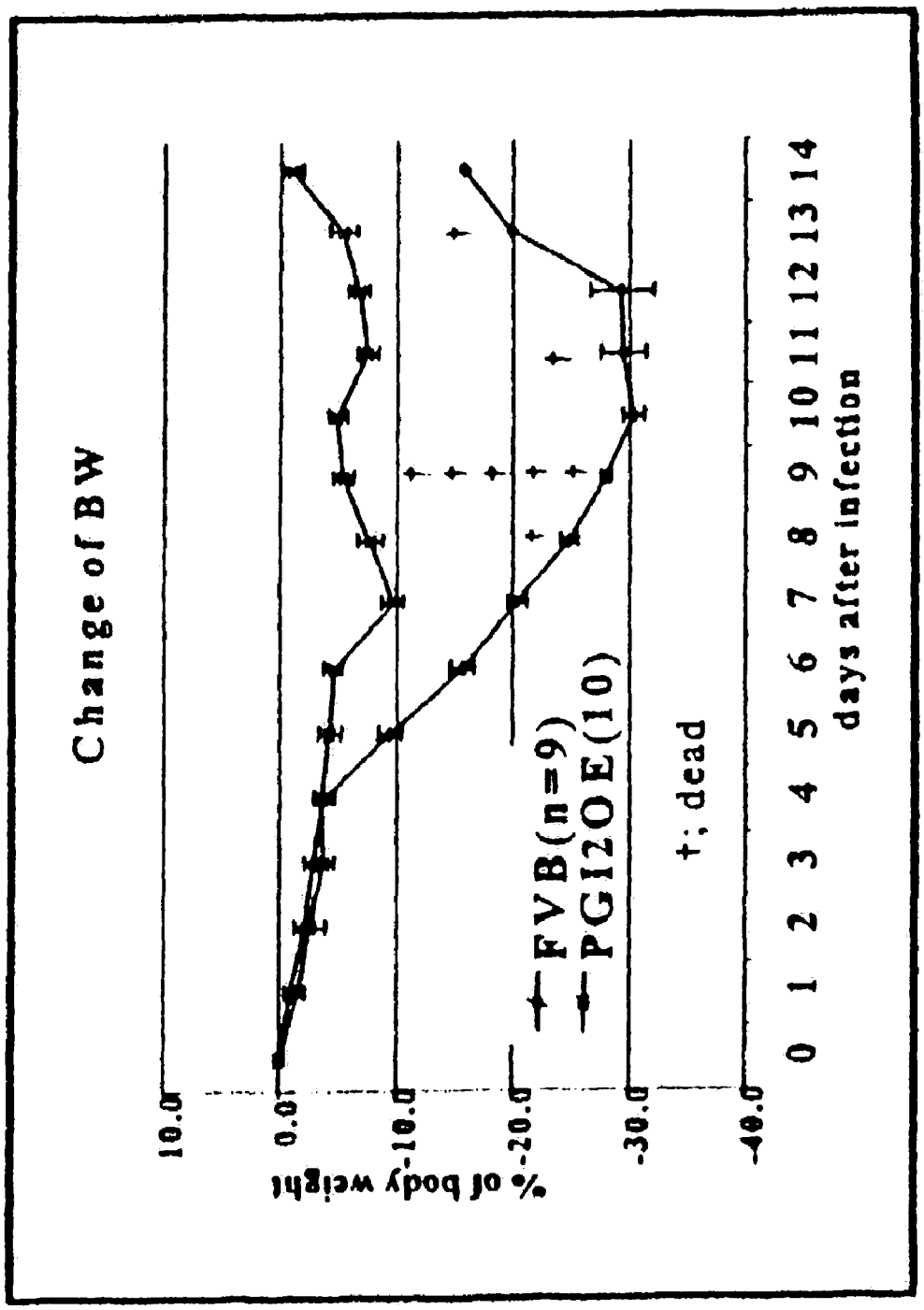
FIG. 1 shows the protective effect resulting from overexpression of the prostacyclin synthase against RSV-induced illness. The wild-type mice are shown in the diamonds. The prostacyclin synthase overexpresssing mice are shown in the squares. The X-axis represents the days after infection and the Y-axis represents the percent of the body weight.

The present invention discloses methods and a kit for treating a respiratory syncytial virus infection. The method comprises providing an infection modulator, and administering a therapeutically effective amount of the infection modulator, wherein the respiratory syncytial virus infection is suppressed or precluded. The kit for suppressing a respiratory syncytial virus infection comprises an infection modulator, an applicator, and a set of instructions. The present invention will be described in detail by referring to the following text.

As used herein, "infection modulator" means any prostacyclin or prostacyclin analog which suppresses a RSV infection. Examples include, but are not limited to, prostacyclin, epoprostenol, UT-15, iloprost, beraprost, and cicaprost. All of the infection modulators may be obtained by chemical synthesis, by methods described in the literature or may be obtained from a commercial source. Accordingly, it is understood that the exogenous infection modulator is being administered to an individual in order to obtain the desired therapeutic effect disclosed herein.

As used herein, "applicator" means any device or tool used during administering a therapeutically effective amount of an infection modulator. Examples include, but are not limited to, subcutaneous needles, surgical needles, aerosol dispensers, intravenous kit and all materials necessary for starting and maintaining an intravenous drip.

As used herein, "therapeutically effective amount" means an amount that is sufficient to bring about the desired medical effect. Although such an amount may produce side effects, an amount that accomplishes the ultimate medical effect of suppressing or precluding a respiratory syncytial virus infection is a therapeutically effective amount. The therapeutically effective amount may vary depending upon certain factors, such as, the particular infection modulator used, the manner of administration, the size and age of the individual being treated, the severity of the RSV infection, the competency of the immune system of the individual, and the like. Effective dose ranges for the infection modulators are disclosed herein. In certain embodiments, a clinician may determine the therapeutically effective amount by considering the above-referenced factors. The manner of application of the infection modulators is disclosed herein. Generally, any suitable manner of administration for any of the specific infection modulators may be employed. Such general manners of administration include intravenous, subcutaneous, oral, and topical administrations.

As used herein, an individual having characteristics which increase the probability of severe symptoms due to a RSV infection means an individual that is less than the age of five or older than the age of 59. Other individuals which are included in this definition include individuals having a suppressed immune system, premature birth, bronchopulmonary dysplasia, and congenital cardiac abnormalities.

In vivo data were obtained by use of a well established murine model. Peebles R., et al., 2001, J. Med. Vir. 63:178–188. The murine model used herein provides a system that is close to the human system. It is believed that the results obtained from the murine model are reasonably correlated to the response of the human system.

Use of Mice Overexpressing Prostacyclin Synthase

Transgenic mice were created with selective pulmonary $PGI_2$ synthase overexpression using a construct of the 3.7 kb human surfactant protein C promoter and the rat $PGI_2$ synthase DNA. $PGI_2$ synthase mRNA of a consistent high-level expression was confirmed by Northern blot. The transgene is expressed predominantly in alveolar lining cells, but also in bronchial epithelial cells. The transgenic mice were of the FVB genetic background. Further, $PGI_2$ synthase enzyme activity was confirmed by measurement of the stable $PGI_2$ metabolite 6-keto PGF alpha. Additionally, the $PGI_2$ metabolite 2,3-dinor-6-keto-PGF alpha is significantly increased in the urine of the $PGI_2$ synthase overexpressing mice (8.11 ng/mg creatinine) compared to the control mice (1.30 ng/mg creatinine). The animals were descendants of a pair of mice previously obtained from Dr. Mark W. Geraci, Division of Pulmonary Sciences and Critical Care Medicine, University of Colorado Health Sciences Center, Campus Box C-272, 420 East Ninth Avenue, Denver, Colo. 80262. Respiratory syncytial virus strain A was the gift of Dr. Robert Chanock, National Institutes of Health, Bethesda, Md.

The genetically altered mice had reduced expression of lung mRNA for TNF beta (day 4 and 6 post infection), TNF alpha (day 6 post infection), IL-6 (day 6 post infection), TGF beta 1 (day 6 post infection), and TGF beta 3 (day 6 post infection). Thus, the genetically altered mice, which overexpress $PGI_2$ synthase and excrete four fold greater levels of $PGI_2$ metabolites in the urine, are protected against weight loss and mortality. Additionally, the altered animals have decreased inflammatory cytokine production in the lung, but still have increased viral clearance.

The level of inflammatory cytokines that are presumed to have important roles in the immune response to viral infections were measured. RNAse protection assays were used to measure the levels of such cytokines. Although those of ordinary skill in the art commonly know RNAse protocols, an RNAse protocol is further described in Peebles, et al., 2000, Am. J. Resp. Crit. Care. Med., 162:676–681.

More specifically, as shown in FIG. 1, the Prostacyclin synthase overexpressing mice were protected against RSV-induced illness. The wild-type mice start losing weight on day 5 and continue to have dramatic weight loss. In the study, eight of the wild-type mice died as a result of the RSV infection. The mice overexpressing the prostacyclin synthase had less severe infections as measured by peak weight loss and they recovered much more quickly from infection compared to the wild-type mice.

Mice overexpressing prostacyclin synthase actually do have higher levels of prostacyclin as compared to wild-type mice. Urine from overexpressing and wild-type mice was collected in order to measure the stable urinary metabolite 2,3-dinor-6-keto-PGF1alpha. This analysis was conducted as described in Dubois RN et al, 1994, J. Clin. Invest. 95:493–498. The prostacyclin synthase overexpressing mice had a 4-fold increase in this urinary metabolite, confirming that $PGI_2$ levels were higher in those mice.

Figure 5:
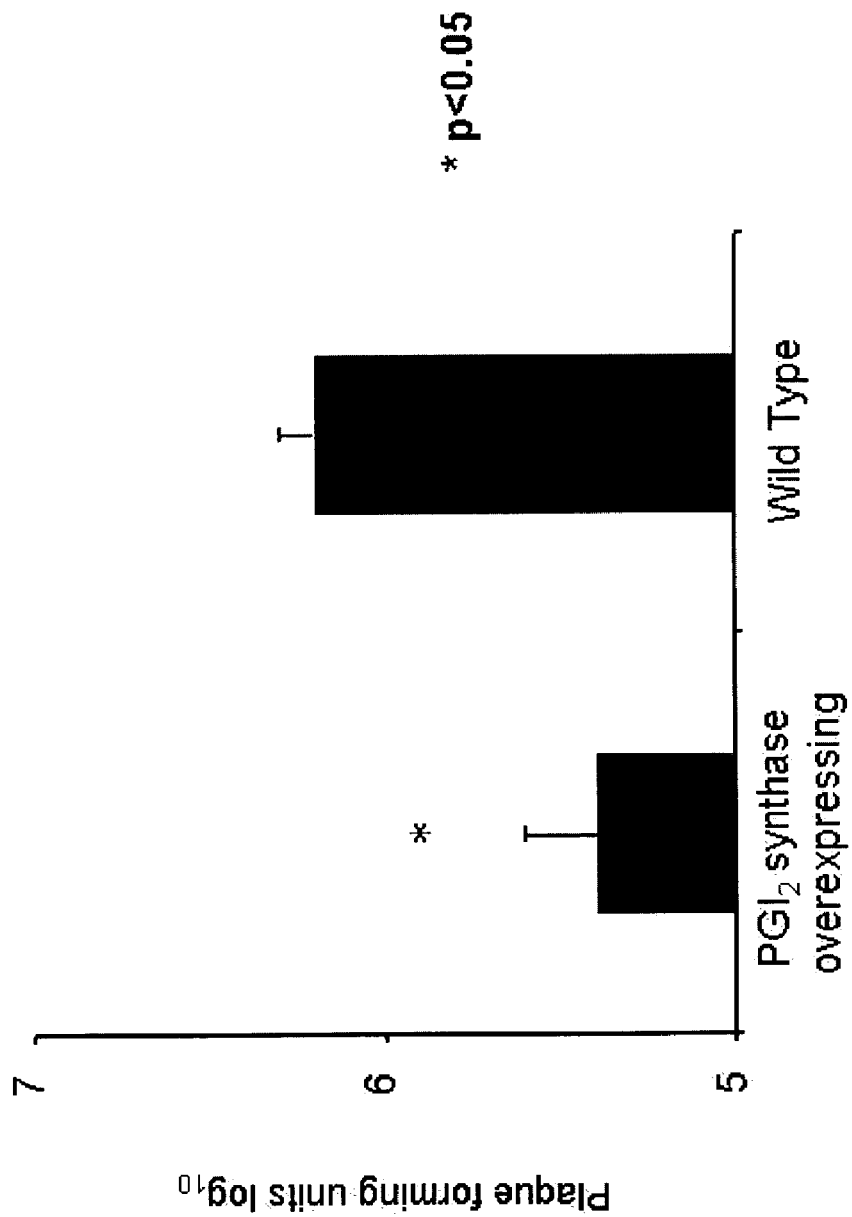
FIG. 5 is a graph showing a decrease in peak viral replication in mice overexpresssing prostacyclin synthase. The plaque forming units $\log_{10}$ is shown for the prostacyclin synthase overexpressing mice and wild-type mice.

Prostacyclin synthase overexpressing mice demonstrate a decrease in the viral titers in the lungs. As shown in FIG. 5, the prostacyclin synthase overexpressing mice had about a ¾ log decrease in peak viral replication compared to the wild-type mice. The decrease in the peak virus titer of RSV in the lungs was demonstrated on day 4 after RSV infection, when such viral titers are normally at their peak. The viral titers were measured according to the protocol described in Graham, et al, 1988, J. Med. Virol. 26:153.

Use of Mice not Overexpressing Prostacyclin Synthase

Genetically altered mice having the BALB/c background were obtained from Charles Rivers Laboratories, 251 Ballardvale Street,. Wilmington, Mass. 01887-1000. Modification to the level of $PGI_2$ was accomplished by introducing indomethacin to the BALB/c mice. Indomethacin is a drug that is used to treat arthritis and other rheumatologic conditions and inhibits the activity of both COX-1 and COX-2 such that the formation of prostanoids, specifically $PGI_2$, are not produced. Indomethacin is given to the mice in their drinking water in order to block the cyclooxygenase enzymes in order to determine the effect of the cyclooxygenase pathway on the immune response to RSV infection. Indomethacin is commercially available from Sigma, Inc. St. Louis, Mo.

Figure 4:
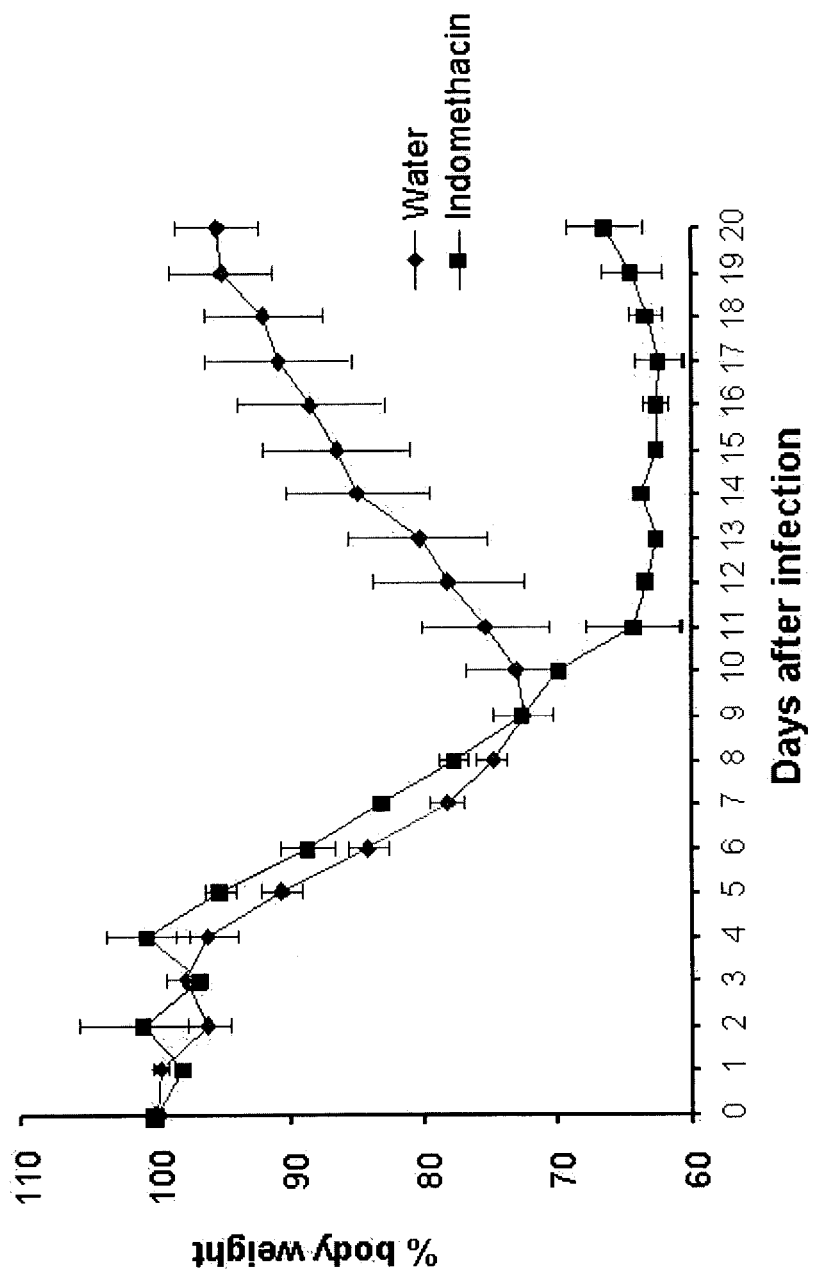
FIG. 4 shows that indomethacin treatment exacerbates and delays recover from RSV-induced illness.

As best seen in FIG. 4, mice treated with indomethacin have a much difference weight loss curve. Within the experiment, BALB/c mice were provided water having indomethacin, 30 micrograms/ml. As shown in FIG. 4, illness peaked on day 11 and the mice receiving indomethacin did not recover their weight. These findings show that cyclooxygenase inhibition led to enhanced illness as a result of RSV infection.

Epoprostenol

Epoprostenol, a synthetic prostacyclin, is an unstable molecule having a halflife of about six minutes. Fink, et al., 1999, Heart Disease, 1:29–40; Cho and Allen, 1978, Prostaglandins, 15:943–954. Eproprostenol is commercially available from Glaxo-Smith K1, 5 Moore Drive, P.O. Box 13398, Research Triangle Park N.C. 27709. Epoprosterol is diluted with sterile water to the desired concentration. Epoprostenol is the sodium salt of prostacyclin. Although the chemical is degraded by light and must be stored at a temperature below 25° C., it may be easily administered to a patient in need thereof.

Epoprostenol is administered intravenously. Due to the short half-life of the drug, and the fact that it is modified in the gastrointestinal tract, the drug is not a candidate to be ingested orally. Epoprostenol is commercially available under the trade name "Flolan." Glaxo-Smith K1, 5 Moore Drive, P.O. Box 13398, Research Triangle Park N.C. 27709. The manufacturer recommends that the drug be reconstituted prior to use intravenously. Reconstitution for use is accomplished by adding a suitable carrier or diluent, which may be in the form of an aqueous or organic solution, dependent upon the manufacturers instructions. Due to the instability of the drug, it should be used within a period of eight hours after it is reconstituted according to the instructions of the manufacturer.

Subsequent to reconstitution, epoprostenol is administered intravenously to a patient in need thereof. In certain embodiments, the recipient takes epoprostenol as a preventative drug prior to being infected by RSV. In other embodiments, the recipient takes epoprostenol as a preventative step prior to the occurrence of symptoms associated with a RSV infection. Preferably, a patient receives epoprostenol in order to relieve the suffering occurring due to the RSV infection.

Epoprostenol is provided to a patient intravenously. In certain embodiments, the infusion rate is initially from about 2 ng/kg/min to about 4 ng/kg/min. The infusion rate may be modified about every 15 minutes. The increase in rate of administration is limited by side effects (flushing, diarrhea, leg pain). The target dose is approximately from about 10 ng/kg/min to about 15 ng/kg/min and periodic dose increases are required to maximize efficacy. In certain embodiments, the infusion rate is modified less frequently than every 15 minutes. In other embodiments, the infusion rate is modified more frequently than about every 15 minutes. Almost all clinical experience with epoprostenol has been limited to the treatment of pulmonary hypertension and in a survey of epoprostenol usage in the United States at nineteen different centers, the dose ranges were from 0.5–270 ng/kg/min. Recently, investigators experienced with the use of this agent suggested the optimal dose to be 22–45 ng/kg/min; lower doses seem to result in diminished effectiveness for pulmonary hypertension whereas higher doses result in excessive toxicity without increased effectiveness. Galie, et al., 2001, Clinics in Chest Medicine, 22:529–537, which is incorporated herein by reference.

Due to mobile intravenous pumps, a patient may receive epoprostenol intravenously for extended periods of time. Preferably, a patient receives epoprostenol during a period of time starting when the patient is suffering from the symptoms of a RSV infection and ending when the symptoms are relieved. In certain embodiments of the present invention, a patient may start receiving epoprostenol prior to RSV infection and end such treatment several days or weeks later without ever suffering with the symptoms of a RSV infection. There are side effects to using epoprostenol. A list of side effects includes flushing, headache, chest pain, sweating, flu-like symptoms, nausea, vomiting, and systemic hypotension. Accordingly, the length of time of infusion and/or the rate of infusion may be modified based upon the response of the patient to the treatment. In certain embodiments of the present invention, the age and physical condition of the patient may warrant a reduction of the rate of infusion to the lowest value previously mentioned. In other embodiments, when the patient is not suffering any side effects from the treatment, the infusion rate is raised to the highest value previously provided.

Iloprost

Iloprost is an analog of epoprostenol, but is more stable. Fink, et al., 1999, Heart Disease, 1:29–40. Although the half life is a relatively short 13 minutes, it is not degraded by light. Kaukinen, et al., 1984, Clin. Pharmacol. Ther., 36:464–469. Iloprost is commercially available from Schering Deutschland GmbH (Germany) at D-13342 Berlin Deutschland. Iloprost is diluted with sterile water to the desired concentration. Iloprost is administered intravenously, orally, or by aerosol. Prior to administration, it is necessary to reconstitute the drug. Reconstitution for use is accomplished by adding a suitable carrier or diluent, which may be in the form of an aqueous or organic solution, dependent upon the manufacturers instructions. Preferably, the drug is reconstituted in a solution having a physiologic pH. In certain embodiments, reconstitution occurs with a solution having a pH from about less than 2 pH units of greater acidity than a physiologic pH to about less than 2 pH units of greater basicity than a physiologic pH.

Subsequent to reconstitution, iloprost is administered intravenously to a patient in need thereof. In certain embodiments, the recipient takes iloprost as a preventative drug prior to being infected by RSV. In other embodiments, the recipient takes iloprost as a preventative step prior to the occurrence of symptoms associated with a RSV infection. Preferably, a patient receives iloprost in order to relieve the suffering occurring due to the RSV infection. Administering iloprost for long periods of time does not appear harmful since studies involving the long-term administration of iloprost to pulmonary hypertension patients showed such administration to be safe. De La Mata, et al., 1994, Arthritis Rheum., 37:1528–1533, which is incorporated herein by reference.

In certain embodiments, Iloprost may be provided to a patient intravenously. In such embodiments, the initial infusion rate is initially 2 ng/kg/min. In other embodiments, the initial infusion rate is from about 0.5 ng/kg/min to about 5 ng/kg/min. The infusion rate may be modified every 15 minutes. In certain embodiments, the infusion rate is modified less frequently than every 15 minutes. In still other embodiments, the infusion rate is modified more frequently than about every 15 minutes. Preferably, the increases to the infusion rate stop when the iloprost reaches 10 ng/kg/min. In certain embodiments, the increases to the infusion rate stop when the iloprost reaches from about 2 ng/kg/min to about 5 ng/kg/min. In other embodiments, the increases to the infusion rate stop when the iloprost reaches about 5 ng/kg/min.

A patient may receive iloprost intravenously for extended periods of time. Higenbottam, et al., 1998, Heart, 79:175–9. Preferably, a patient receives iloprost during a period of time starting when the patient is suffering from the symptoms of a RSV infection and ending when the symptoms are relieved. In certain embodiments of the present invention, a patient may start receiving iloprost prior to RSV infection and end such treatment several days or weeks later without ever suffering with the symptoms of a RSV infection. The length of time of infusion and/or the rate of infusion may be modified based upon the response of the patient to the treatment. In certain embodiments of the present invention, the age and physical condition of the patient may warrant a reduction of the rate of infusion to the lowest value previously mentioned. In other embodiments, when the patient is not suffering any side effects from the treatment, the infusion rate is raised to the highest value previously provided.

Iloprost may also be administered orally. Although oral administration is possible, less than 20% of the iloprost will reach the systemic circulation. Krause, et al., 1984, Drug Metab., 12:645–651. When administered orally, preferably, the iloprost dose is 100 micrograms. In certain embodiments, the oral iloprost dose is from about 150 micrograms to about 50 micrograms. In other embodiments, the oral iloprost dose is about 50 micrograms. Belch, et al., 1995, Ann. Rheum. Dis., 54:197–200, which is incorporated herein by reference. Preferably, when iloprost is administered orally, a singe dose is given 2 times per day. In certain embodiments, the iloprost is administered at least two times per day. In other embodiments, the iloprost is administered no more than two times per day. A patient's reaction to the treatment is to be considered in order to modify the amount and/or frequency with which the patient receives iloprost.

In certain embodiments, iloprost is administered as an aerosol. Use of iloprost as an aerosol has been previously reported. Olschewski, et al., 1996, Ann Intern Med., 124: 820–824; Mikhail, et al., 1997, Eur. Heart J., 18:1499–1504. In certain embodiments, an iloprost aerosol of about 50 micrograms/day is given. In other embodiments, an iloprost aerosol having a concentration of from about 200 micrograms/day to about 50 micrograms/day is given. When iloprost is given as an aerosol, doses should be given 6–12 times per day. In certain embodiments, the doses are given at a frequency of about 2 hours between doses. In other embodiments, while the aerosol treatment continues, at least one dose is given during each 4 hour period. In other embodiments, the aerosol is administered at least six times per 24 hour period. When iloprost is administered as an aerosol, it may be dispensed from any mobile or non-portable dispenser that is capable of discharging an aerosol. Examples of devices used to discharge aerosols include, but are not limited to, hand held dischargers, similar to those commonly used by asthma patients, emphysema patients, and patients requiring mechanical ventilation.

UT-15

UT-15, also known as 15AU81, is another stable prostacyclin analog. UT-15 has a longer half-life than epoprostenol. UT-15 may be administered intravenously or subcutaneously. UT-15 has previously been safely used on patients to treat another disease. Patterson, et al., 1995, Am. J. Cardiol., 75:26A-33A. UT-15 is commercially available from United Therapeutics, Silver Spring, Md. 20910. Reconstitution of the drug is not necessary. UT-15 is diluted into sterile water to the desired concentration.

UT-15 may be administered intravenously to a patient in need thereof. In certain embodiments, the recipient takes UT-15 as a preventative drug prior to being infected by RSV. In other embodiments, the recipient takes UT-15 as a preventative step prior to the occurrence of symptoms associated with a RSV infection, but subsequent to infection. Preferably, a patient receives UT-15 in order to relieve the suffering occurring due to the RSV infection.

UT-15 is provided to a patient intravenously. Preferably, in certain embodiments, the infusion rate is initially 10 ng/kg/min. In other embodiments, the initial infusion rate is from about 5 ng/kg/min to about 20 ng/kg/min. In still other embodiments, the initial infusion rate is 20 ng/kg/min. The infusion rate may be modified about every 15 minutes. In certain embodiments, the infusion rate is modified less frequently than every 15 minutes. In still other embodiments, the infusion rate is modified more frequently than every 15 minutes. Preferably, the increases to the infusion rate stop when the UT-15 reaches 10 ng/kg/min. In certain embodiments, the increases to the infusion rate stop when the UT-15 reaches from about 5 ng/kg/min to about 15 ng/kg/min. In other embodiments, the increases to the infusion rate stop when the UT-15 reaches 15 ng/kg/min.

Due to mobile devices used for distributing components intravenously, a patient may receive UT-15 intravenously for extended periods of time. Methods of drug delivery intravenously, for all components disclosed within this patent application, include microinfusion pumps. Preferably, a patient receives UT-15 during a period of time starting when the patient is suffering from the symptoms of a RSV infection and ending when the symptoms are relieved. In certain embodiments of the present invention, a patient may start receiving UT-15 prior to RSV infection and end such treatment several days or weeks later without ever suffering with the symptoms of a RSV infection. The length of time of infusion and/or the rate of infusion may be modified based upon the response of the patient to the treatment. In certain embodiments of the present invention, the age and physical condition of the patient may warrant a reduction of the rate of infusion to the lowest value previously mentioned. In other embodiments, when the patient is not suffering any side effects from the treatment, the infusion rate is raised to the highest value previously provided.

UT-15 may also be administered subcutaneously. Methods of administering UT-15 subcutaneously include, but are not limited to, subcutaneous inject with a needle and administration with a subcutaneous catheter. When administered subcutaneously, the UT-15 dose is about 10 ng/kg/min. In certain embodiments, the UT-15 dose is from about 5 ng/kg/min to about 20 ng/kg/min. In other embodiments, the UT-15 dose is 5 ng/kg/min. A patient's reaction to the treatment is to be considered in order to modify the amount and/or frequency with which the patient receives UT-15.

As further described below in Example 9, treating BALB/c mice with various concentrations of UT-15 resulted in an increase percentage of survival. These results suggest that the protection the prostacyclin synthase overexpressing mice had against the RSV infection was related to those mice having overexpression of prostacyclin and not some other unrelated factor of those transgenic animals.

Thus, the results provided herein indicate that infection modulators, such as prostacyclin, epoprostenol, UT-15, Ilaprost, beraprost, and cicaprost, are useful in the treatment of viral infections in mice. Because the data shows that the genetically altered prostacyclin synthase overexpressing mice and the mice receiving UT-15 exerted antiviral activity against RSV, it is expected that the other infection modulators disclosed herein will be useful for the treatment of RSV infections. This conclusion is reached since the two separate sources of infection modulators were capable of exerting antiviral activity against RSV.

Beraprost

Beraprost is a stable prostacyclin analog that may be used to treat a RSV infection. Beraprost is administered orally as beraprost sodium. Beraprost is commercially available from Kaken Pharmaceutical Co. Ltd., 28-8 Honko mayome-Zchome Bunkyo-kv 113-8650 Tokyo 113-8650, Japan. The compound is available in tablets and administered orally. Oral ingestion for this compound, and other compounds disclosed herein that are administered orally, is accomplished by ingesting either a solid structure (pill, or dissolvable coating containing the component) or a liquid solution containing the active component to be administered orally.

An individual may undertake treatment for a RSV infection prior to or after an actual infection. In certain embodiments, the individual, or recipient, takes beraprost as a preventative drug prior to being infected by RSV. In other embodiments, the recipient takes beraprost after RSV infection, but prior to the occurrence of symptoms associated with a RSV infection. Preferably, a patient receives beraprost in order to relieve the suffering occurring due to the RSV infection.

As discussed above, beraprost is administered orally. When administered orally, preferably, the beraprost dose is about 60 micrograms per day. In certain embodiments, the oral beraprost dose is from about 60 micrograms/day to about 180 micrograms/day. In other embodiments, the beraprost dose is from about 90 micrograms/day to about 120 micrograms/day. In still other embodiments, the oral beraprost dose is from about 60 micrograms/day to about 90 micrograms/day.

Preferably, when beraprost is administered orally, a singe dose is given about 4 times per day. In certain embodiments, the beraprost is administered at least 4 times per day. In other certain embodiments, the beraprost is administered more than 4 times per day. A patient's reaction to the treatment is to be considered in order to modify the amount and/or frequency with which the patient receives iloprost.

The use of infection modulators, as described herein, results in the suppression or preclusion of RSV infections. A RSV infection is precluded when the preventative activity block, prohibit, interrupt or delay the infection. A RSV infection is suppressed when the incidence, intensity or severity of the infection is reduced. A RSV infection is also suppressed when the infection is inhibited, or restrained from a usual course or action. Accordingly, when describing a RSV infection, the words precluded or suppressed have the usual medical meaning. As further described herein, determining that the RSV infection is suppressed may be accomplished in a number of ways. With regard to mammals, a determination that a RSV infection is suppressed may be made by monitoring the weight retention of the subject, monitoring the mortality of the subject, monitoring the body temperature of the subject, or tracking the level of certain chemicals in the blood of the subject. Further examples of determining that a RSV infection has been suppressed include, but are not limited to, identifying a level of a molecular derivative, such as $pO_2$ in a biological sample of the subject. Methods of measuring the level of $pO_2$ are well known in the art. The standard ways of assessing severity of illness involve indices, known to those of ordinary skill in the art, that include parameters such as need for intubation and length of stay in the hospital or intensive care unit.

Use of Genetically Altered Mice not having the IP Receptor

Transgenic mice have been created which lack the prostacyclin receptor, abbreviated IP. Transgenic mice in which the IP receptor was knocked out were obtained from Dr. Garret A. FitzGerald of the University of Pennsylvania, 153 Johnson Pavillion, 3620 Hamilton Walk, Philadelphia, Pa. 19104-6084.

Binding of $PGI_2$ to its receptor activates adenylate cyclase in a dose-dependent manner, increasing the production of cyclic adenosine monophosphate (cAMP). Breyer, et al., 2000, Ann. NY Acad. Sci. 905:221. This increase in intracellular cAMP mediates $PGI_2$'s effect of inhibiting platelet aggregation, and dispersing existing platelet aggregates both in vitro and in human circulation. Breyer, et al., 2000, Ann. NY Acad. Sci. 905:221. Northern blot analysis reveals that IP receptor mRNA is expressed to the greatest degree in the thymus, while high level of IP receptor mRNA expression is also found in spleen, heart, lung, and neurons in the dorsal root ganglia. IP is also expressed in T cells of mice, along with the $PGE_2$ receptor (EP) subtypes and the thromboxane receptor (TP). Narumiya, et al., 1999, Physiol. Rev. 79:1193. To our knowledge, the function of IP in murine T lymphocytes has not been investigated. IP has also been found in kidney smooth muscle and epithelial cells. Komhoff, et al., 1998, Kidney Int. 54:1899. There are not published reports detailing examination of lung epithelium for IP. Thus, IP has been located on several different cell types and full cellular localization is not complete.

Figure 9:
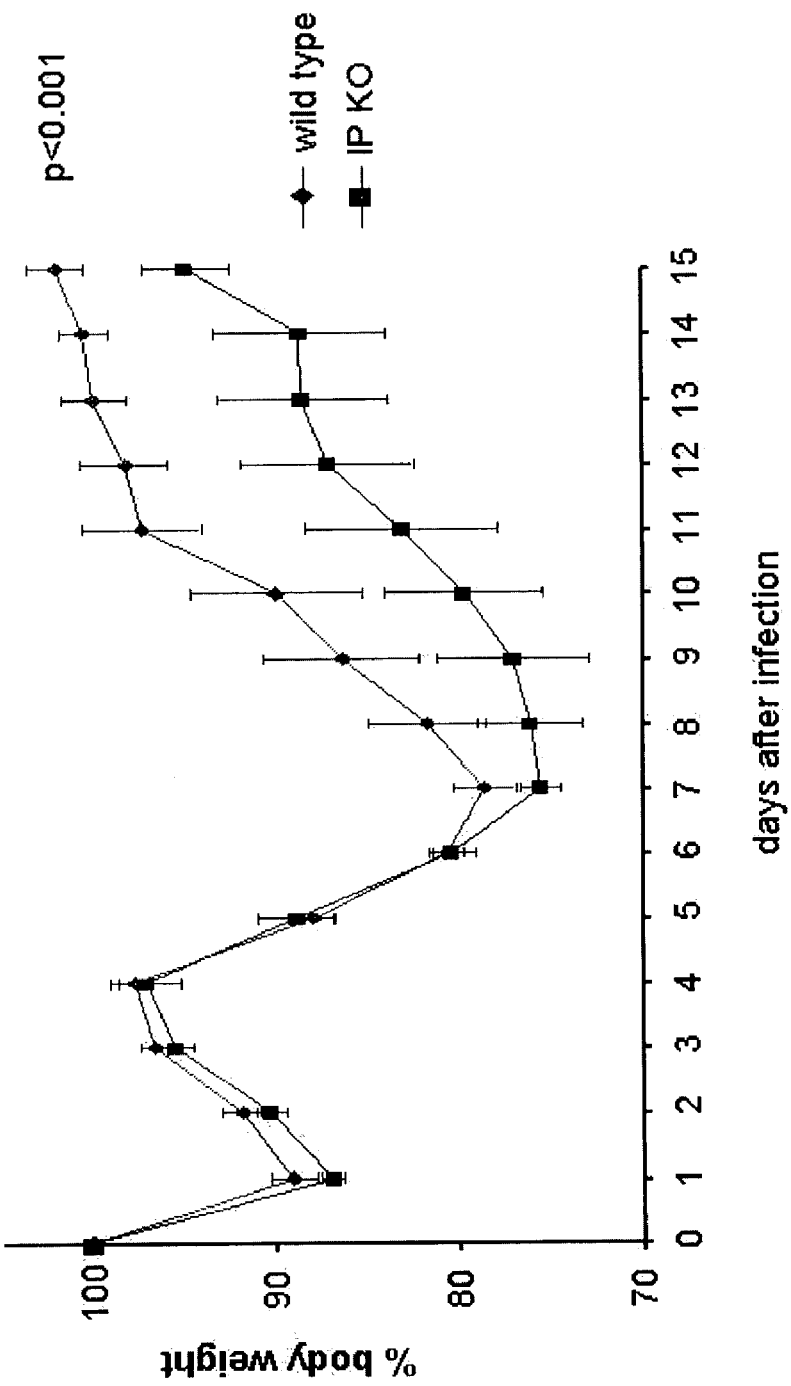
FIG. 9 is a graph showing that RSV infection causes enhanced body weight loss in IP knockout mice. Wild-type mice are represented by the diamonds. Genetically altered mice in which the IP receptor has been knocked out are represented by the squares. The X-axis shows the days after RSV infection. The Y-axis provides the percent body weight of the animal.

As further described in the Example 10, RSV infection caused enhanced disease in IP knockout mice. Although the IP knockout mice are on a C57BL/6 background, which differs from the background of the prostacyclin synthase overexpressing mice, the IP knockout mice demonstrated a significant reduction in percent of body-weight and a lengthened recovery period with respect to wild-type mice, as best seen in FIG. 9.

A kit for suppressing a RSV infection is disclosed by the present invention. In certain embodiments, a kit includes an infection modulator, an applicator, and a package for containing the infection modulator and applicator. In other embodiments, a kit includes an infection modulator, an applicator, a set of instructions, and a package for containing those items. The kit is designed to allow easy administration of the infection modulator in a non-hospital setting.

Thus, although there have been described particular embodiments of the present invention of a new and useful method and kit for treating respiratory syncytial virus, it is not intended that such references be construed as limitations upon the scope of this invention except as set forth in the following potential claims. Further, the scope of this invention shall not be bound by mechanism or theory.

All citations referenced herein, including scientific publications, patents and other publications, are hereby incorporated by reference as a part of the specification. Further, although there have been described certain steps or components used in the preferred embodiments, it is not intended that such steps or components be construed as limitations upon the scope of this invention except as set forth in the following potential claims.

The following Examples are provided for illustration, but not limitation, of the present invention.

EXAMPLES

Example 1

Treatment of RSV Infection with Prostacyclin

The effects of prostacyclin were monitored in an experimental respiratory syncytial virus infection murine model. The experiments used genetically altered mice that overexpress prostaglandin $I_2$ ($PGI_2$) synthase. The animals were descendants of a pair of mice previously obtained from Dr. Mark W. Geraci, Division of Pulmonary Sciences and Critical Care Medicine, University of Colorado Health Sciences Center, Campus Box C-272, 420 East Ninth Avenue, Denver, Colo. 80262. Respiratory syncytial virus strain A was the gift of Dr. Robert Chanock, National Institutes of Health, Bethesda, Md. The transgenic mice were created with selective pulmonary $PGI_2$ synthase overexpression using a construct of the 3.7 kb human surfactant protein C promoter and the rat $PGI_2$ synthase DNA. $PGI_2$ synthase mRNA of a consistent high-level expression was confirmed by Northern blot. The transgene is expressed predominantly in alveolar lining cells, but also in bronchial epithelial cells. The transgenic mice were of the FVB genetic background. Further, $PGI_2$ synthase enzyme activity was confirmed by measurement of the stable $PGI_2$ metabolite 6-keto PGF alpha. Additionally, the $PGI_2$ metabolite 2,3-dinor-6-ketoPGF1 alpha is significantly increased in the urine of the $PGI_2$ synthase overexpressing mice (8.11 ng/mg creatinine) compared to the control mice (1.30 ng/mg creatinine).

The genetically altered mice and control mice were (1) either male or female, (2) had a body weight in the range of 20–24 grams, and (3) were 8–12 weeks old at the time of infection with RSV. The genetically altered mice and control mice were anesthetized with ketamine and xylazine, as described in Peebles, et al., 2001, J. Med. Virol. 63:178–88, which is incorporated herein by reference. The mice were intranasally infected with $10^7$ pfu of RSV strain A. American Type Culture Collection, Manassas, Va.

The following parameters were monitored during each experiment: total body weight and viability.

The overexpression of $PGI_2$ synthase was found to suppress the symptoms associated with respiratory syncytial virus infection. More specifically, the genetically altered mice were protected against the weight loss and mortality associated with the RSV-induced illness. The genetically altered mice suffered a weight loss of 10% of the pre-infection weight. The control mice lost 30% of the pre-infection weight, as shown in FIG. 1. Furthermore, eight of the nine control mice died during the experiment while none of the genetically altered mice died.

Figure 2:
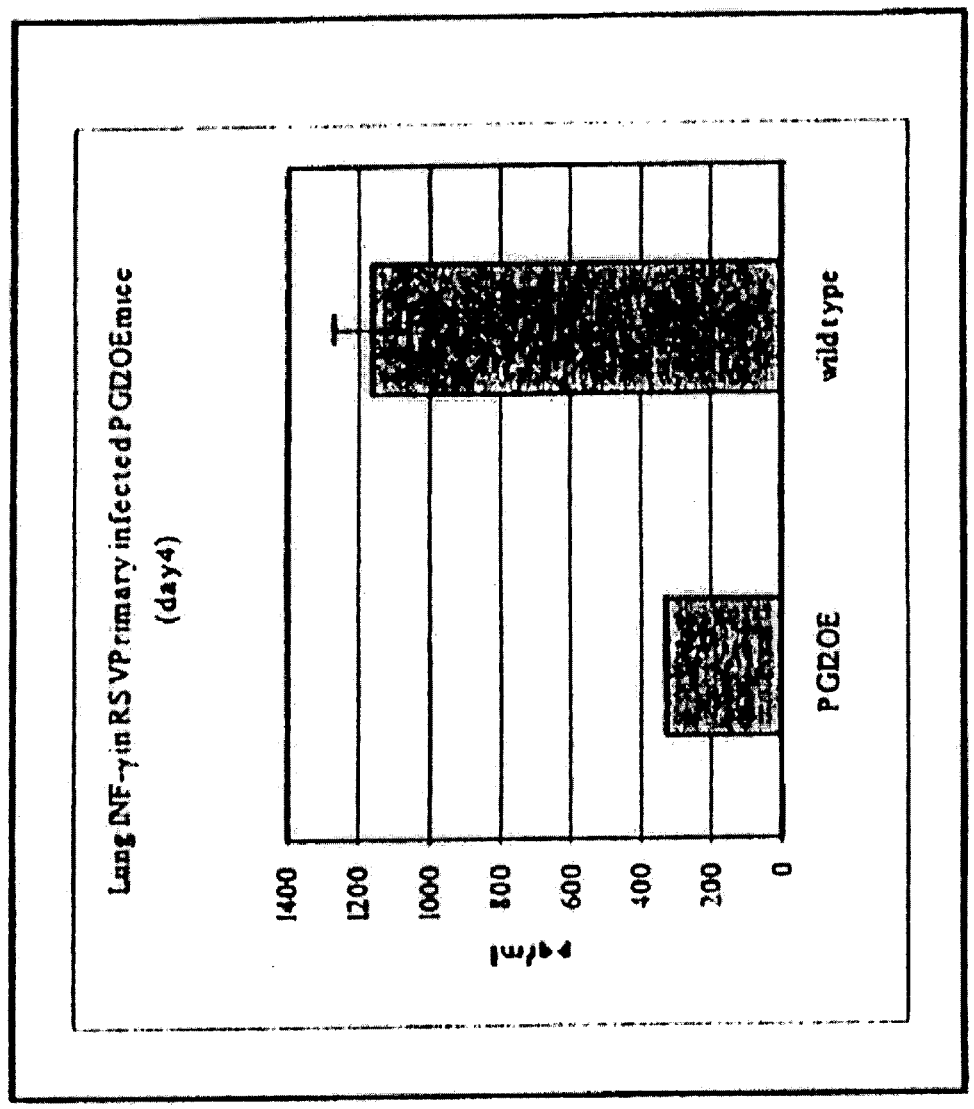
FIG. 2 shows a comparison, between genetically altered mice and control mice, of the level of lung INF gamma during RSV post infection.

The genetically altered mice had a decreased RSV replication. Viral replication was assessed by plaque assay on day 4, the peak of viral replication. The plaque assay protocol is detailed in Graham, et al., 1988, J. Med. Virol., 26:153–162, which is incorporated herein by reference. TNF alpha, tumor necrosis factor alpha, and IFN gamma, interferon gamma, levels in lung homogenates were also measured. The measurement assay is detailed in Peebles, et al., 2000, J. Infect. Dis., 182:671–7, which is incorporated herein by reference. As shown in FIG. 2, the genetically altered mice had significantly decreased IFN gamma levels in lung homogenates compared to the control mice.

Example 2

Treatment of a Patient Having a RSV Infection with Intravenous Administration of Epoprostenol Epoprostenol, a synthetic prostacyclin, is commercially available from Glaxo Wellcome (Research Triangle Park, N.C.) as Flolan. Epoprostenol is diluted in sterile water to the desired concentration. Epoprostenol is administered to a patient intravenously. The patient has characteristics which increase the probability of severe symptoms due to a RSV infection. Reconstitution of the drug occurs as directed by the recommendations of the manufacturer. More specifically, reconstitution for use is accomplished by adding a suitable carrier or diluent, which may be in the form of an aqueous or organic solution, dependent upon the manufacturers instructions.

Once a medical professional prepares the intravenous drip, epoprostenol is initially infused at a rate of 2 ng/kg/min. The infusion rate increases by increments of 2 ng/kg/min every 15 minutes. Infusion increases stop when the epoprostenol reaches 45 ng/kg/min. Long-term infusion occurs by using a mobile pump that allows the patient to continue to be mobile. Infusion at the treatment level indicated above is continued for a period of time until the patient is not suffering from the common symptoms of a RSV infection.

Example 3

Treatment of a Patient Having a RSV Infection with Subcutaneous Administration of UT-15

UT-15, a prostacyclin analog, is commercially available from United Therapeutics, Silver Spring, Md. 20910. UT-15 is diluted in sterile water to the desired concentration. UT-15 is subcutaneously administered to a patient having a RSV infection. Reconstitution of the drug is not required. A solution containing UT-15 is placed in a syringe. The syringe is fitted with a needle for injection of the solution into the patient. The solution containing UT-15 contains one dose of UT-15. One dose consists of a solution containing a sufficient amount of UT-15 so that the patient receives, by subcutaneous injection, 10 ng/kg/min of UT-15 per kg of total body weight of the patient. This subcutaneous injection of UT-15 is continuous until the patient is not suffering from the common symptoms of a RSV infection.

Example 4

Treatment of a Patient Having a RSV Infection with Intravenous Administration of Iloprost Iloprost is commercially available from Schering Deutschland GmbH (Germany). Iloprost is diluted in sterile water to the desired concentration. A patient having a RSV infection and needing relief from the symptoms of the infection receives iloprost intravenously. Although reconstitution of the drug occurs as directed by the recommendations of the manufacturer, reconstitution preferably occurs with a solution having a physiologic pH.

Once a medical professional prepares the patient to receive an intravenous drip, iloprost is initially infused at a rate of 2 ng/kg/min. The infusion rate increases by increments of 2 ng/kg/min every 15 minutes. Increases to the rate of infusion stop when the iloprost reaches 4 ng/kg/min. Long-term infusion occurs by using a mobile pump that allows the patient to continue to be mobile. Infusion at the treatment level indicated above continues for a period of time until the patient is not suffering from the common symptoms of a RSV infection.

Example 5

Treatment of a Patient not Having a RSV Infection with Orally Administered Beraprost as a Preventative Measure Beraprost sodium is commercially available from Kaken Pharmaceutical Co. Ltd, Tokyo, Japan. An individual not yet infected with RSV, but wanting to suppress or avoid the symptoms of a RSV infection orally ingests beraprost sodium. The individual consumes 60 micrograms of beraprost sodium per day with this dose divided by a frequency of 4 doses per day. The individual continues to receive the treatment orally until the condition which places the individual at "high risk" for a RSV infection passes (i.e. individual is no longer an infant).

Example 6

Weight-Loss in the BALB/c Mouse due to RSV Infection

Figure 3:
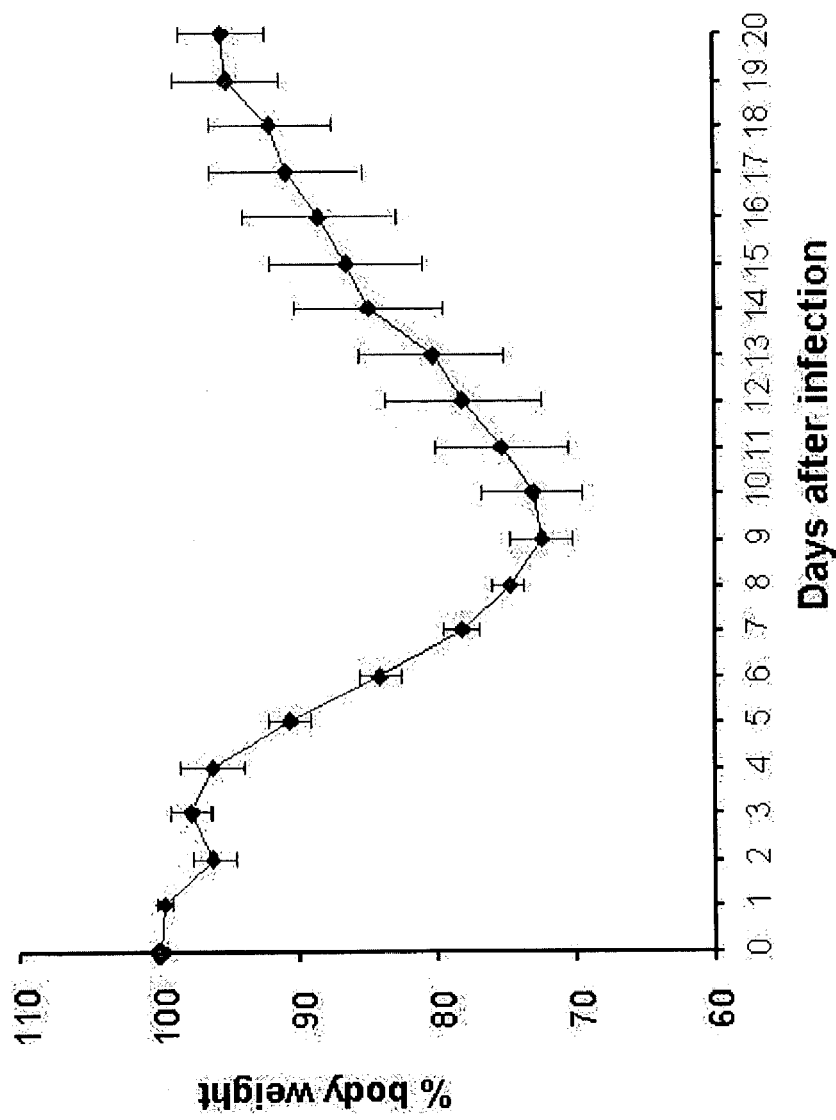
FIG. 3 shows the course of RSV-induced weight loss in the BALB/c mouse.

Female BALB/c mice that are 8–10 weeks of age and that weigh approximately 20 grams were used to determine the amount of weight loss that results from an RSV infection. The BALB/c mice were infected with RSV strain A as described in Example 1. Subsequent to infection, the mice received water in their drinking bottles to drink during the course of an infection. On day 5, the mice started to lose weight and the peak of illness as measured by maximal weight loss occurred on day 9. In this experiment, the mice that were given water to drink had a peak weight loss to about 75% of their baseline weight, or a 25% weight loss. These mice then recovered and were fully back to baseline by day 19 after infection. FIG. 3 is an example of a typical body weight curve that occurs with RSV induced illness. On the Y-axis is the body weight as a percentage of the pre-infection weight. This curve is very reproducible although factors such as the strain of the mouse and the viral load administered can alter the severity and duration of illness.

Example 7

Investigation of Mechanism by which Prostacylcin Synthase Overexpression Exerts Protective Effect Intracellular cytokine analysis of the lung cells from the prostacyclin synthase overexpressing and wild-type mice, after infection, was performed. Wild-type mice having a BALB/c background, previously described, and transgenic mice overexpressing prostacyclin synthase, previously described, were infected with RSV strain A as described in Example 1. The mice were sacrificed on days 4, 7, and 10 after infection with RSV. The lungs were removed and then were ground in a wire mesh strainer so that single cell suspension of the cells in the lungs could be obtained, as further described in Peebles, et al., 2001, J. Med. Virol. 63:178–88, which is incorporated herein by reference. This suspension was then subjected to Ficoll purification to eliminate the red blood cells and lung debris and the mononuclear cell layer was isolated and enriched, as further described in Peebles, et al., 2001, J. Med. Virol. 63:178–88. The cells were then counted and then incubated in Golgi stop overnight without stimulation, as further described in Peebles, et al., 2001, J. Med. Virol. 63:178–88. After washing the cells they were stained for the cell surface markers CD4, CD8, and NK1.1. Peebles, et al., 2001, J. Med. Virol. 63:178–88. The cell surface markers are commercially available from Pharmingen, 10975 Torreyana Rd, San Diego, Calif. 92121. NK1.1 is the antibody used to identify NK cells in FVB mice. After washing, the cell membrane was permeabilized and then stained for IFN-gamma and. TNF-alpha to determine the cytokines produced in the mononuclear cells in the lungs. Peebles, et al., 2001, J. Med. Virol. 63:178–88. Again, this was a time course experiment, measuring IFN-gamma and TNF-alpha in the CD4, CD8, and NK cell populations on days 4, 7, and 10.

Figure 6:
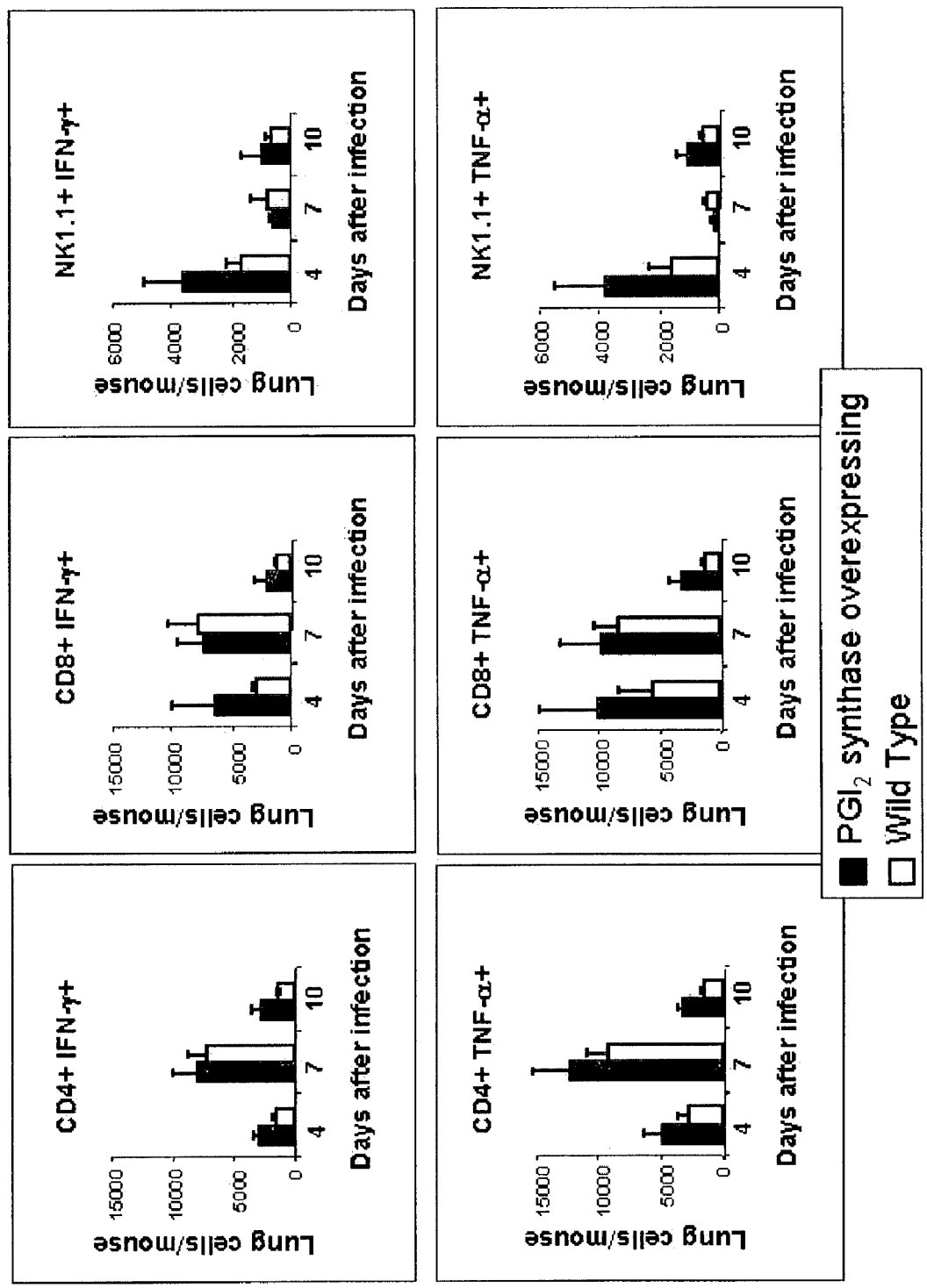
FIG. 6 is a series of graphs showing the levels of specifically identified molecules at specifically identified points in time after infection. Intracellular cytokine analysis of the lung cells from the RSV infected prostacyclin synthase overexpressing and wild type mice was performed. The mice were sacrificed on days 4, 7, and 10 after infection. Lung cells were stained for the cell surface markers CD4, CD8, and NK1.1. IFN-gamma and TNF-alpha in the CD4, CD8, and NK cell populations were measured on days 4, 7, and 10. The prostacyclin synthase overexpressing mice are shown in the shaded bars and the wild type mice are shown in the non-shaded bars.

As shown in FIG. 6, prostacyclin synthase overexpressing mice are shown with the white bars and the wild-type mice are shown with the shaded bars. The CD4 cell population in the two panels on the left show a very small increase in the IFN-gamma staining CD4 cells on day 4 as shown in the top left panel, and a similar increase in the TNF-alpha staining CD4 cells shown in the bottom left with very little difference between the two groups on day 7 and 8. However, there was about a doubling of CD8 producing IFN-gamma producing mononuclear lung cells on day 4 in the prostacyclin synthase overexpressing mice compared to the wild-type mice and a similar finding in the CD8 cells producing TNF-alpha cells. The same pattern held true in the IFN-gamma and TNF-alpha producing NK cells, about a two fold increase in these cell populations in the prostacyclin overexpressing mice compared to the wild type controls. This increase in IFN-gamma producing CD8 and NK cells may be part of the explanation of the decrease in peak viral titers seen in the prostacyclin synthase overproducing mice.

Example 8

Insertion of a Micro-infusion Pump into a Mouse

In order to insert a micro-infusion pump into a mouse, the skin of the back, slightly posterior to the scapulae will be shaved and washed with ethanol. Subcutaneous implantation is technically the easiest and least invasive procedure. The usual site for subcutaneous implantation of Azlet pumps in mice is on the back, slightly posterior to the scapulae. Pumps are commercially available at: Alzet Osmotic Pumps, Durect Corporation, P.O. Box 530, Cupertino, Calif. 95015-0530. Absorption of the compound placed in the pump by local capillaries results in systemic administration. For subcutaneous pump implantation, the following steps are performed:

Step 1. Shave and wash the skin over the implantation site.

Step 2. Make a suitable incision adjacent to the site chosen for pump placement (a mid-scapular incision in this protocol).

Step 3. Insert a hemostat into the incision, and, by opening and closing the jaws of the hemostat, spread the subcutaneous tissue to create a pocket for the pump (e.g. 1 cm longer than the pump). Avoid making the pocket too large, as this will allow the pump to turn around or slip down on the flank of the animal. The pump will not rest immediately beneath the incisional wound, for this may interfere with the healing of the incision.

Step 4. Insert a filled pump into the pocket, delivery portal first. This minimizes interaction between the compound delivered and the healing of the incision.

Step 5. Close the wound with wound clips or sutures.

Example 9

UT-15 Protection against RSV-Induced Mortality

Figure 7:
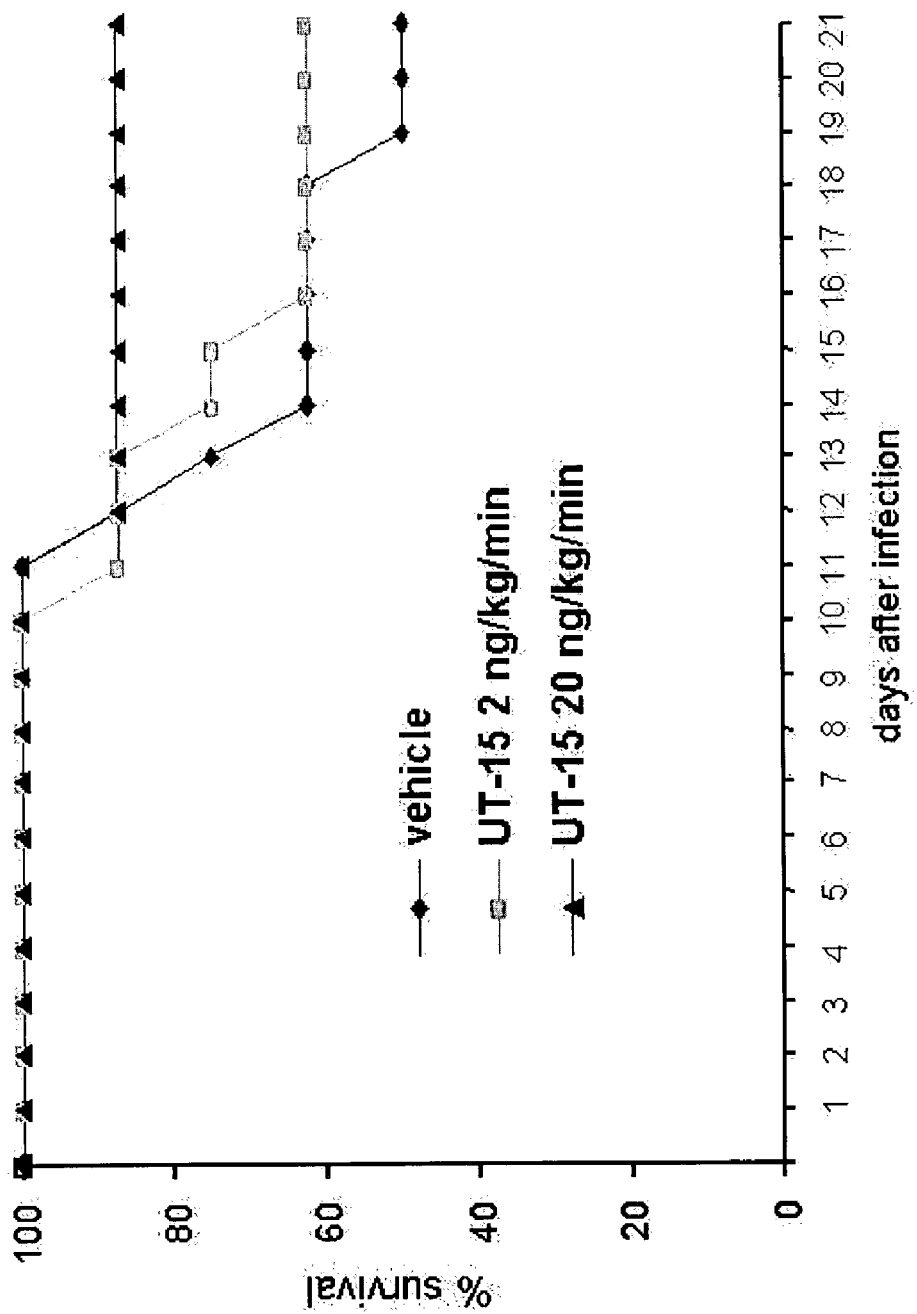
FIG. 7 is a graph showing that UT-15 protects against RSV-induced mortality. Percent survival is shown on the Y-axis. Days after an RSV infection is shown on the X-axis. Mice not receiving any UT-15 are represented by the diamonds. Mice receiving 2.0 ng/kg/min are represented by the squares. Mice receiving 20 ng/kg/min are represented by the triangles.

A micro-infusion pump system was inserted into a mouse as previously described in Example 8. After the micro-infusion pump was in place, UT-15 was administered subcutaneously for two weeks starting on the day prior to infection. The BALB/c mice received either different concentrations of UT-15 or water only, as indicated below. BALB/c mice were infected with RSV strain A as described in Example 1. There were 8–10 mice per group. The weight of each mouse was monitored on a daily basis. The mice were put on a scale to measure their weight. As best seen in FIG. 7, the BALB/c mice, which are treated with 20 ng/kg/min dose of UT-15, demonstrated the best survival percentage. BALB/c mice treated with a 2.0 ng/kg/min dose of UT-15 showed the next best survival percentage. It was found that there was a 50% mortality rate in the BALB/c mice which did not receive UT-15. It was also further noted that the mice treated with 2.0 ng/kg/min of UT-15, of the mice which survived, the recovery period was quicker than those which did not receive UT-15. The same was true of the mice treated with 20 mg/kg/min dose of UT-15.

Figure 8:
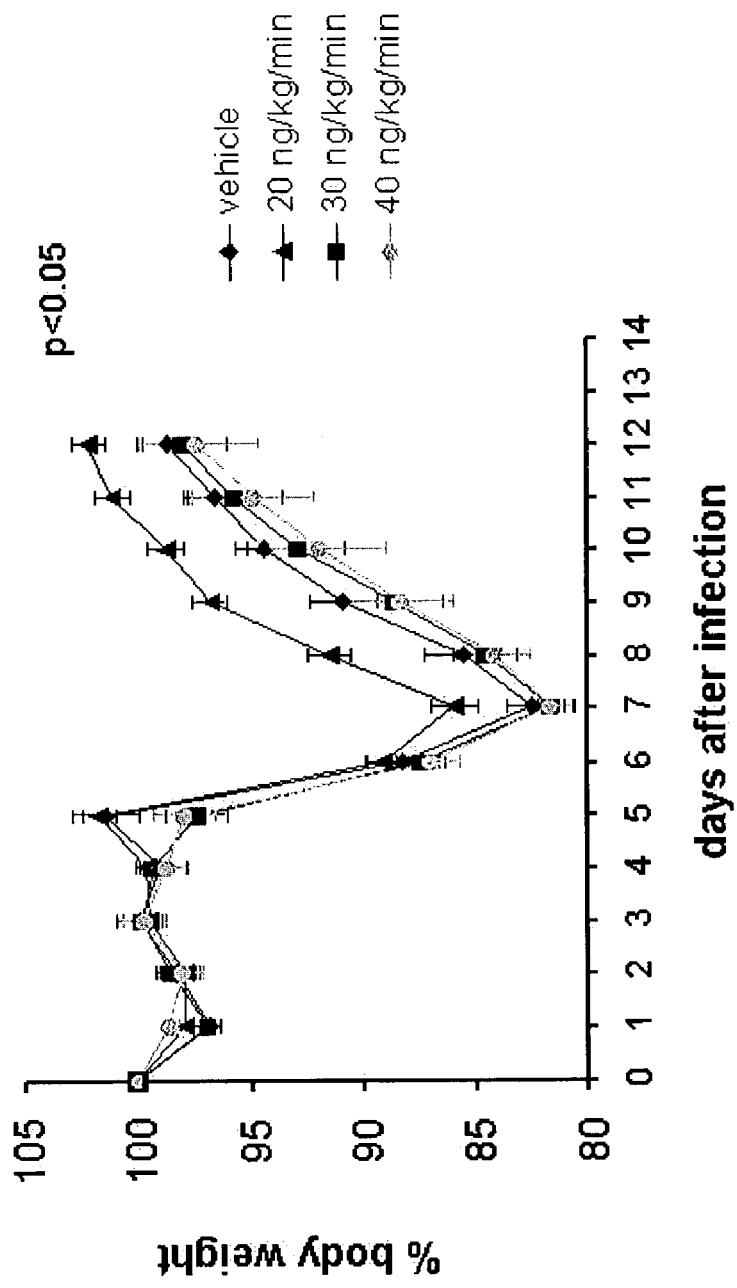
FIG. 8 is a graph showing that UT-15 protects against RSV-induced illness. On the X-axis is shown the days after RSV infection. The Y-axis shows the percent of body weight of the mice. Mice not receiving UT-15 are represented by the diamonds. Mice receiving 20 ng/kg/min of UT-15 are represented by the triangles. Mice receiving 30 ng/kg/min of UT-15 are represented by the squares. Mice receiving 40 ng/kg/min of UT-15 are represented by the circles.

Mice having received micro-infusion pumps received infusion of either water of some concentration of UT-15 for a period of 2 weeks after starting the day prior to RSV infection. As best seen in FIG. 8, the mice receiving a concentration of 20 ng/kg/min of UT-15 displayed the quickest recovery period for body weight. Also shown are the percentage of body weight for each of the animals on each given day for the other animals either receiving no UT-15 or other concentrations of UT-15.

Example 10

RSV Infection of Genetically Altered Mice not Having the IP Receptor

Transgenic mice in which the IP receptor was knocked out were obtained from Dr. Garret FitzGerald of the University of Pennsylvania, 153 Johnson Pavillion, 3620 Hamilton Walk, Philadelphia, Pa. 19104-6084.

Wild-type mice C57BL6 (Jackson Laboratory, 600 Main Street Bar Harbor Me. 04609) and IP knockout mice having a C57BL6 background, were infected with RSV strain A as described in Example 1. The body weight of all mice was monitored on a daily basis, as described in Example 9. As shown in FIG. 9, the percent body weight from the pre-infection is shown on the Y-axis. The wild-type mice, shown as white diamonds, had a typical illness curve with a peak weight loss of 20% on day 7.

The genetically altered mice, represented by white squares, had a 25% weight loss on day 7 and a delayed recovery from the illness.

The genetically altered IP knockout mice additionally showed a delay in viral clearance. As further described in Johnson, et al., 1997, J. Virol. 72:2871–2880, which is incorporated herein by reference, four or six days following RSV challenge, mice were sacrificed by $CO_2$ narcosis and cervical dislocation. The lungs were removed, placed in EMEM-10% FCS, and quick-frozen in an alcohol-dry ice bath. RSV titers in the lungs were measured by standard plaque assays using 80% confluent HEp-2 monolayers. Briefly, lungs were quick-thawed and ground with a mortar and pestle. Serial 10-fold dilutions of lung supernatants were used to infect the monolayers in triplicate, and cultures were grown under 0.75% methylcellulose in EMEM-10% FCS. Cells were formalin fixed 5 days after infection and stained with hematoxylin and eosin, and plaques were counted under a dissecting microscope. Data are represented as the geometric mean $\log_{10}$ PFU per gram of lung tissue±standard error of the mean (SEM) at the dilution producing more than five plaques per well. On day 4 after RSV infection, wild-type mice had 5.57 plaque forming units $\log_{10}$ as compared to the IP knockout mice which had 6.19 plaque forming units $\log_{10}$. Further, on day 6 post-RSV infection, the wild-type mice had 4.7 plaque forming units $\log_{10}$ as compared to the IP knockout mice having 4.1 plaque forming units $\log_{10}$.

What is claimed is:

1. A method of suppressing a respiratory syncytial virus infection, comprising:
   providing an individual having characteristics which increase the probability of severe symptoms due to a respiratory syncytial virus infection;
   providing an infection modulator, wherein the infection modulator is selected from a group consisting of prostacyclin, epoprostenol, UT-15, iloprost, and beraprost; and
   administering a therapeutically effective amount of the infection modulator,
   wherein the respiratory syncytial virus infection is suppressed.

2. The method of claim 1, wherein the infection modulator is epoprostenol.

3. The method of claim 2 wherein administering further comprises administering intravenously.

4. The method of claim 3, wherein administering a therapeutically effective amount of the infection modulator further comprises administering from about 10 ng/kg/min to about 15 ng/kg/min of the infection modulator.

5. The method of claim 1, wherein the infection modulator is UT-15.

6. The method of claim 5, wherein administering further comprises administering with a method selected from a group consisting of intravenous, subcutaneous, subcutaneous catheter, and microinfusion pump.

7. The method of claim 5, wherein administering a therapeutically effective amount of the infection modulator further comprises administering from about 5 ng/kg/min to about 20 ng/kg/min of the infection modulator.

8. The method of claim 1, wherein the infection modulator.

9. The method of claim 8, wherein administering further comprises administering with a method selected from a group consisting of intravenous, oral, and aerosol.

10. The method of claim 9, wherein the aerosol is administered at least six times per 24 hour period.

11. The method of claim 8, wherein administering a therapeutically effective amount of the infection modulator further comprises administering from about 2 ng/kg/min to about 5 ng/kg/min of the infection modulator.

12. The method of claim 1, wherein the infection modulator is beraprost.

13. The method of claim 12, wherein administering further comprises ingesting the beraprost orally.

14. The method of claim 13, wherein administering a therapeutically effective amount of the infection modulator further comprises administering from about 60 micrograms/day to about 180 micrograms/day of the infection modulator.

15. A method of treating respiratory syncytial virus in an individual in need thereof comprising administering to the patient a therapeutically effective amount of a prostacyclin analog.

* * * * *